United States Patent [19]

Schumann

[11] Patent Number: Plant 5,375

[45] Date of Patent: Dec. 18, 1984

[54] GERANIUM PLANT NAMED OLYMP

[75] Inventor: Ingeborg Schumann, Bad Ems, Fed. Rep. of Germany

[73] Assignee: Pelargonien-Fischer KG, Hillscheid, Fed. Rep. of Germany

[21] Appl. No.: 548,223

[22] Filed: Nov. 2, 1983

[51] Int. Cl.[3] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of geranium plant named Olymp, and particularly characterized by its semi-double flower form and vermilion red flower color, fast rooting, zoned leaves, large flowerhead, cultivation below 12° C., and by its excellent branching.

3 Drawing Figures

The present invention comprises a new and distinct cultivar of geranium, botanically known as *Pelargonium zonale,* and hereinafter referred to by the cultivar name Olymp.

Olymp is a product of planning breeding program which had the objective of creating new geranium cultivars having orange-red flower color, leave zonation, short plant height, fast rooting, good branching, durable flowers, and stable peduncles.

Olymp was originated from a hybridization made in a controlled breeding program in Hillscheid, Federal Republic of Germany in 1979. The female parent was the unpatented cultivar Dondo Royal, having red semi-double flowers, a large flowerhead, but inferior branching. The male parent of Olymp was a cultivar derived from the self-breeding of the unpatented cultivar PAC® Alex, a cultivar having good branching and red semi-double flowers carried on long peduncles.

Olymp was discovered and selected as one flowering plant within the progeny of the stated cross by Ingeborg Schumann on June 27, 1980 in a controlled environment in Hillscheid, Federal Republic of Germany.

The first act of asexual reproduction of Olymp was accomplished when vegetative cuttings were taken from the initial selection in January, 1981 in a controlled environment in Hillscheid, Federal Republic of Germany by a technician working under formulations established and supervised by Ingeborg Schumann. Horticultural examination of selected units initiated in the Spring of 1981, and continuing in 1982 has demonstrated that the combination of characteristics as herein disclosed for Olymp are firmly fixed and are retained through successive generations of a sexual reproduction.

Olymp has not been observed under all possible environmental conditions. The phenotype may vary significantly with variations in environment such as temperature, light intensity, and day length. The following observations, measurements, and comparisons describe plants grown in Hillscheid, Federal Republic of Germany under greenhouse conditions which approximate those generally used in commercial practice.

The following traits have been repeatedly observed and are determined to be basic characteristics of Olymp, which in combination distinguish this geranium as a new and distinct cultivar:

1. Dutch vermilion red flower color.
2. Zoned leaves.

3. Fast rooting.
4. Semi-double flower form.
5. Olymp can be cultivated below 12° C.
6. No growth treatment is necessary for quality plant production.
7. Relatively long peduncle with anthocyan.
8. Large flowerhead (umbel).
9. Excellent branching, producing an average of 6.3 branches per plant.

Of the many commercial cultivars known to the present inventor, the most similar in comparison to Olymp are the unpatented cultivars PAC® Alex and Empress. Reference is made to attached Chart A which compares certain characteristics of Olymp to those same characteristics of PAC® Alex, with Chart A additionally including comparisons with the unpatented cultivars Vesuv and Rubin. In general comparison to PAC® Alex, Olymp has a shorter, more stable peduncle, foliage zonation, different flower color, earlier response, a larger flowerhead, and better branching. In comparison to Empress, Olymp has smaller leaves, better branching, shorter internode length, and shorter plant height.

The accompanying photographic drawings show typical flower and foliage characteristics of Olymp, with colors being as true as possible with illustrations of this type. Sheet 1 is a color photograph of a potted plant of Olymp. Sheet 2 is a relatively enlarged color photograph of the flowers, buds, and foliage, and Sheet 3 is a black and white print of the underside of typical leaves of Olymp.

In the following description color references are made to The Royal Horticultural Society Colour Chart, with parallel or alternative values from Horticultural Color Chart (H.C.C.) being shown in certain instances. The color values were determined between 2:30 and 2:50 P.M. on Aug. 12, 1983 under 20,000 Klux at Hillscheid, Federal Republic of Germany.

CLASSIFICATION

Botanical: A hybrid of the genus *Pelargonium l'hert.*
Commercial: Olymp.

INFLORESCENCE

Umbel:

*Average diameter.*—114 mm.
*Average depth.*—88 mm.
*Peduncle length.*—231 mm.

*Pedicel length.*—23 mm.

Corolla:

*Average diameter.*—52 mm.

*Form.*—Semi-double, nearly round.

*Color (general tonality from a distance of three meters).*—R.H.S. 33A, H.C.C. 717/1, with small blue-red eye.

*Color (abaxial).*—R.H.S. 40A, H.C.C. 717.

*Color (adaxial).*—H.C.C. 717/2.

Bud:

*Shape.*—Elliptic.

*Color (abaxial).*—Melange red.

Reproductive organs:

*Androecium.*—Monodelphous, 8–9 stamens.

*Gynoecium.*—5–6 lobed stigma, color red; style, red in color.

Spring flowering response period: In Hillscheid, Federal Republic of Germany in 1982, 80% of plants with at least 1 flower opened 13 weeks after planting of unrooted cuttings.

Outdoor flower production: The flower count in Hillscheid, Federal Republic of Germany in 1982 was between 63 and 66 flowers per plant for June through October observation period.

Durability: Shatter resistance good.

PLANT

Foliage:

*Form.*—Kidney shaped.

*Margin.*—Bicrenate.

*Color(abaxial).*—Medium green.

*Color (zonation).*—Brown, weak to medium zonation.

*Tolerance to botrytis.*—Good.

General appearance and form:

*Internode length.*—40 mm.

*Branching pattern.*—Good; 16.3 branches per plant.

*Height.*—280 mm., Medium.

Chart A

| | Corolla Color | Hillscheid Spring Flowering Response | Branching (number of branches) |
|---|---|---|---|
| PAC ® Alex | RHS 44 B | 55% | 5.6 |
| Vesuv | RHS 43 B small pink eye | 50% | 3.0 |
| Rubin | RHS 33 A inside white | 75% | 2.8 |
| Olymp | RHS 33 A small blue-red eye | 80% | 6.3 |

| | Internode Length | Plant Height | Zonation | Umbel Average Diameter |
|---|---|---|---|---|
| PAC ® Alex | 40 mm | 270 mm | no | 106 mm |
| Vesuv | 23 mm | 220 mm | no | 109 mm |
| Rubin | 31 mm | 250 mm | weak | 108 mm |
| Olymp | 40 mm | 280 mm | weak to medium | 114 mm |

| | Average Depth | Peduncle Length | Pedicel Length | Corolla Average Diameter |
|---|---|---|---|---|
| PAC ® Alex | 74 mm | 250 mm | 24 mm | 49 mm |
| Vesuv | 73 mm | 200 mm | 30 mm | 51 mm |
| Rubin | 73 mm | 213 mm | 39 mm | 54 mm |
| Olymp | 88 mm | 231 mm | 23 mm | 52 mm |

I claim:

1. A new and distinct cultivar of geranium plant named Olymp, as described and illustrated, and particularly characterized by its semi-double flower form and vermilion red flower color, fast rooting, zoned leaves, large flowerhead, cultivation below 12° C., and by its excellent branching.

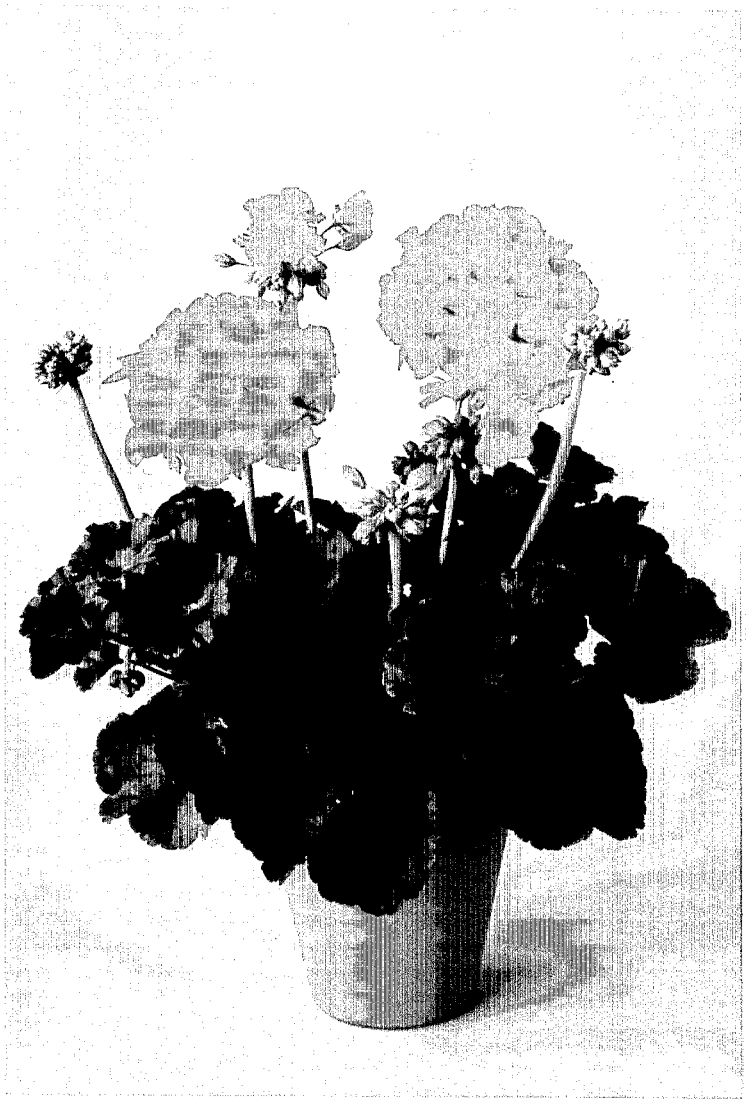

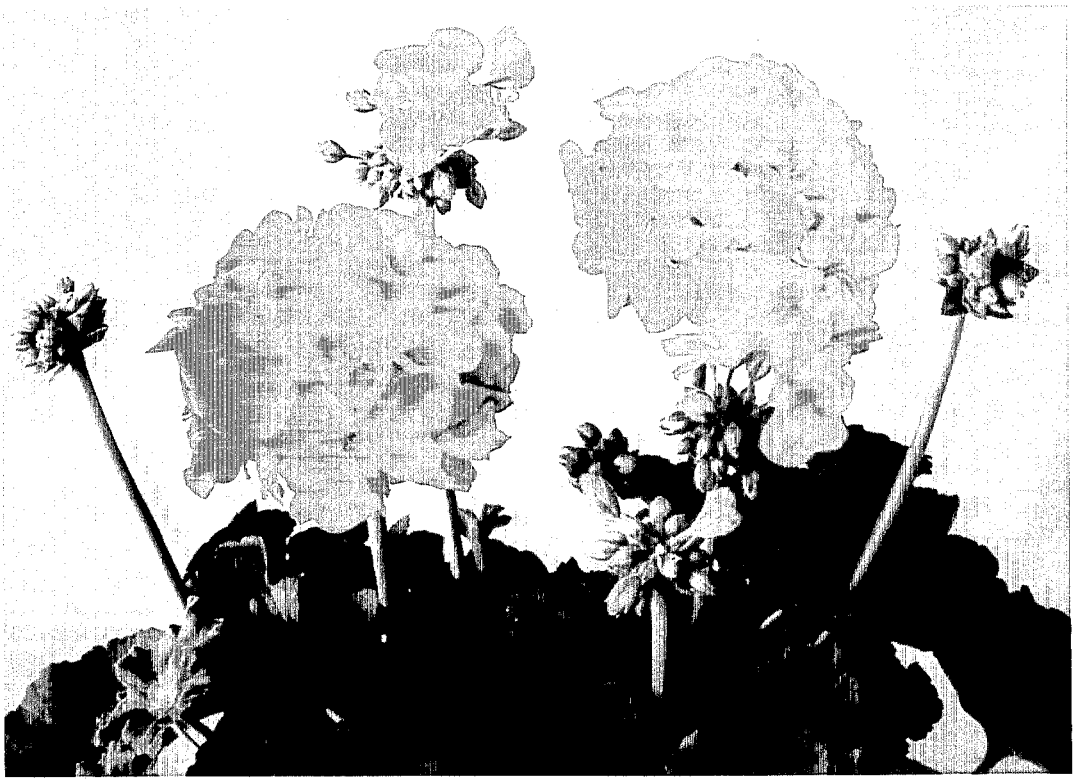

O l y m p
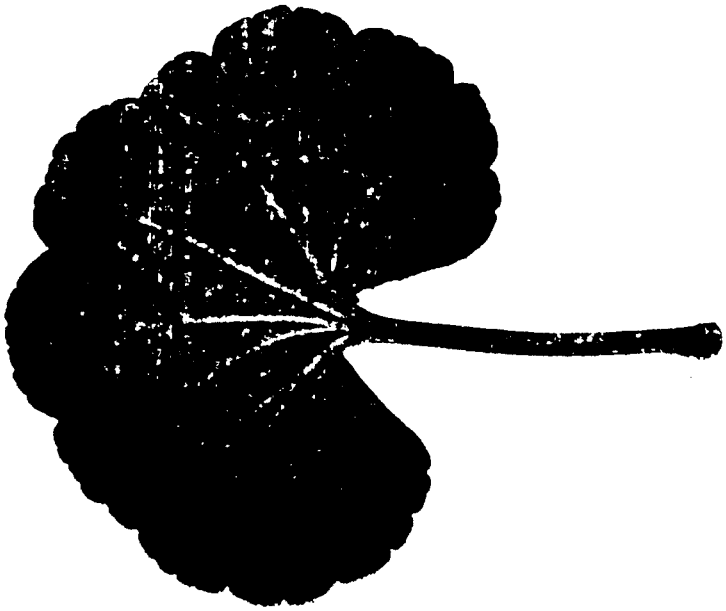
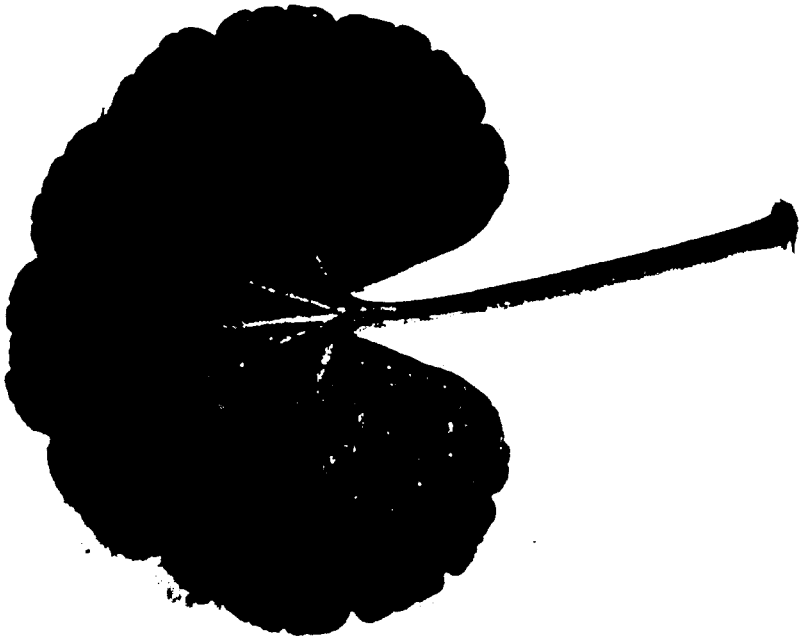

* * * * *